(12) United States Patent
Fabian et al.

(10) Patent No.: US 10,219,931 B2
(45) Date of Patent: Mar. 5, 2019

(54) OBSTRUCTION DEVICE

(71) Applicant: Easynotes Ltd., Kfar Truman (IL)

(72) Inventors: Izhak Fabian, Kfar Truman (IL); Nir Altman, Kfar Etzion (IL); Steven Haas, Kochav Yair (IL); Yoav Hirsch, Modiin (IL)

(73) Assignee: Easynotes Ltd., Kfar Truman (IL)

( * ) Notice: Subject to any disclaimer, the term of this patent is extended or adjusted under 35 U.S.C. 154(b) by 162 days.

(21) Appl. No.: 14/363,800

(22) PCT Filed: Nov. 8, 2012

(86) PCT No.: PCT/US2012/064050
§ 371 (c)(1),
(2) Date: Jun. 8, 2014

(87) PCT Pub. No.: WO2013/070838
PCT Pub. Date: May 16, 2013

(65) Prior Publication Data
US 2014/0350588 A1 Nov. 27, 2014

Related U.S. Application Data

(60) Provisional application No. 61/557,478, filed on Nov. 9, 2011.

(51) Int. Cl.
*A61B 17/12* (2006.01)
*A61B 17/00* (2006.01)
*A61F 5/00* (2006.01)

(52) U.S. Cl.
CPC ...... *A61F 5/0079* (2013.01); *A61B 17/12031* (2013.01); *A61B 17/12036* (2013.01);
(Continued)

(58) Field of Classification Search
CPC ............ A61F 5/0079; A61B 17/12022; A61B 17/12027; A61B 17/12031;
(Continued)

(56) References Cited

U.S. PATENT DOCUMENTS

| 4,598,699 A | 7/1986 | Garran |
| 4,694,827 A | 9/1987 | Weiner |

(Continued)

FOREIGN PATENT DOCUMENTS

| DE | 3116462 | 12/1982 |
| WO | 2010/129162 | 11/2010 |
| WO | 2011/146729 | 11/2011 |

OTHER PUBLICATIONS

PCT Written Opinion PCT/US2012/064050, dated Mar. 11, 2013.

*Primary Examiner* — Christopher L Templeton
(74) *Attorney, Agent, or Firm* — Dekel Patent Ltd.; David Klein

(57) ABSTRACT

An obstruction device includes an obstruction disc mounted on a proximal portion of a shaft. Anchoring members are disposed on the shaft on a proximal side of the obstruction disc. The anchoring members include a pair of loops which are orthogonal to each other, one being a longitudinal member and the other a latitudinal member. One or more support struts, which include one or more loops, are disposed on a distal side of the obstruction disc.

7 Claims, 3 Drawing Sheets

(52) U.S. Cl.
CPC .. *A61B 17/12099* (2013.01); *A61B 17/12159* (2013.01); *A61B 17/12172* (2013.01); *A61B 17/1204* (2013.01); *A61B 17/12022* (2013.01); *A61B 17/12027* (2013.01); *A61B 2017/00592* (2013.01); *A61B 2017/00606* (2013.01); *A61B 2017/00615* (2013.01); *A61B 2017/00818* (2013.01); *A61B 2017/1205* (2013.01)

(58) Field of Classification Search
CPC .......... A61B 17/12036; A61B 17/1204; A61B 17/12099; A61B 17/12131; A61B 17/12172; A61B 17/0057; A61B 2017/00592; A61B 2017/00615; A61B 2017/00818; A61B 17/1214; A61B 17/12104; A61B 17/12109; A61B 17/12122; A61B 2017/00575; A61B 2017/0061; A61B 2017/00601; A61B 2017/00681; A61B 2017/00743
See application file for complete search history.

(56) References Cited

U.S. PATENT DOCUMENTS

| | | | |
|---|---|---|---|
| 4,832,055 A * | 5/1989 | Palestrant | A61F 2/01 128/899 |
| 5,527,338 A * | 6/1996 | Purdy | A61B 17/12022 606/108 |
| 5,944,738 A * | 8/1999 | Amplatz | A61B 17/0057 606/213 |
| 6,086,577 A * | 7/2000 | Ken | A61B 17/12022 606/1 |
| 6,152,144 A * | 11/2000 | Lesh | A61B 17/0057 128/898 |
| 6,180,848 B1 * | 1/2001 | Flament | A61B 17/0057 606/151 |
| 6,193,708 B1 * | 2/2001 | Ken | A61B 17/12022 606/1 |
| 6,558,400 B2 | 5/2003 | Deem | |
| 7,020,531 B1 | 3/2006 | Colliou | |
| 7,288,099 B2 | 10/2007 | Deem | |
| 7,288,101 B2 | 10/2007 | Deem | |
| 7,399,271 B2 * | 7/2008 | Khairkhahan | A61B 17/12022 600/16 |
| 7,503,922 B2 | 3/2009 | Deem | |
| 7,510,559 B2 | 3/2009 | Deem | |
| 7,803,195 B2 | 9/2010 | Levy | |
| 7,862,574 B2 | 1/2011 | Deem | |
| 7,909,838 B2 | 3/2011 | Deem | |
| 8,075,577 B2 | 12/2011 | Deem | |
| 8,080,025 B2 | 12/2011 | Deem | |
| 8,226,602 B2 | 7/2012 | Quijana | |
| 9,078,660 B2 * | 7/2015 | Boutillette | A61B 17/12022 |
| 2002/0111647 A1 * | 8/2002 | Khairkhahan | A61B 17/0057 606/200 |
| 2003/0055451 A1 * | 3/2003 | Jones | A61B 17/12022 606/200 |
| 2003/0057156 A1 * | 3/2003 | Peterson | A61B 17/12022 210/645 |
| 2003/0093097 A1 * | 5/2003 | Avellanet | A61B 17/12022 606/157 |
| 2003/0093108 A1 * | 5/2003 | Avellanet | A61B 17/12022 606/194 |
| 2003/0195553 A1 * | 10/2003 | Wallace | A61B 17/12022 606/200 |
| 2004/0019388 A1 | 1/2004 | Starkebaum | |
| 2004/0034366 A1 | 2/2004 | Van Der Burg et al. | |
| 2004/0044361 A1 * | 3/2004 | Frazier | A61B 17/0057 606/200 |
| 2004/0122452 A1 | 6/2004 | Andreas | |
| 2005/0154252 A1 * | 7/2005 | Sharkey | A61B 17/12022 600/37 |
| 2005/0222488 A1 * | 10/2005 | Chang | A61B 17/00234 600/37 |
| 2005/0277966 A1 * | 12/2005 | Ewers | A61B 17/0401 606/153 |
| 2006/0155323 A1 * | 7/2006 | Porter | A61B 17/12022 606/200 |
| 2006/0199995 A1 * | 9/2006 | Vijay | A61B 17/12022 600/37 |
| 2006/0264980 A1 * | 11/2006 | Khairkhahan | A61B 17/0057 606/153 |
| 2007/0100369 A1 | 5/2007 | Cragg | |
| 2007/0149994 A1 | 6/2007 | Sosnowski | |
| 2007/0282349 A1 | 6/2007 | Deem | |
| 2007/0161846 A1 * | 7/2007 | Nikolic | A61N 1/05 600/16 |
| 2007/0179527 A1 * | 8/2007 | Eskuri | A61B 17/0057 606/213 |
| 2007/0213740 A1 | 9/2007 | Deem | |
| 2007/0213748 A1 | 9/2007 | Deem | |
| 2007/0250083 A1 | 10/2007 | Deem | |
| 2007/0265658 A1 * | 11/2007 | Nelson | A61B 17/00234 606/213 |
| 2008/0140099 A1 | 6/2008 | Ghabriel | |
| 2009/0216262 A1 | 8/2009 | Burnett | |
| 2010/0010532 A1 * | 1/2010 | Vallabhaneni | A61B 17/0057 606/198 |
| 2010/0100107 A1 * | 4/2010 | Duggal | A61B 17/12022 606/151 |
| 2010/0256659 A1 | 10/2010 | Aguirre | |
| 2010/0274085 A1 | 10/2010 | Mugan | |
| 2011/0082495 A1 * | 4/2011 | Ruiz | A61B 17/0057 606/213 |
| 2011/0000495 A1 | 6/2011 | Priplata | |
| 2011/0144560 A1 | 6/2011 | Gagner | |
| 2011/0152899 A1 | 6/2011 | Deem | |
| 2011/0288581 A1 * | 11/2011 | Paul, Jr. | A61B 17/0057 606/213 |
| 2012/0065667 A1 * | 3/2012 | Javois | A61B 17/12122 606/213 |
| 2012/0095385 A1 | 4/2012 | Babkes | |
| 2012/0095483 A1 * | 4/2012 | Babkes | A61F 5/0079 606/153 |
| 2012/0116447 A1 * | 5/2012 | Stanley | A61B 17/0057 606/213 |
| 2012/0191125 A1 | 7/2012 | Babkes | |
| 2012/0265030 A1 | 10/2012 | Li | |
| 2012/0271337 A1 * | 10/2012 | Figulla | A61B 17/0057 606/191 |
| 2012/0323160 A1 * | 12/2012 | Babkes | A61F 5/0033 604/9 |
| 2013/0018413 A1 * | 1/2013 | Oral | A61B 17/12186 606/213 |
| 2015/0250482 A1 * | 9/2015 | Slaughter | A61B 17/12036 606/200 |
| 2016/0081695 A1 * | 3/2016 | Kassab | A61B 17/12022 606/213 |

* cited by examiner

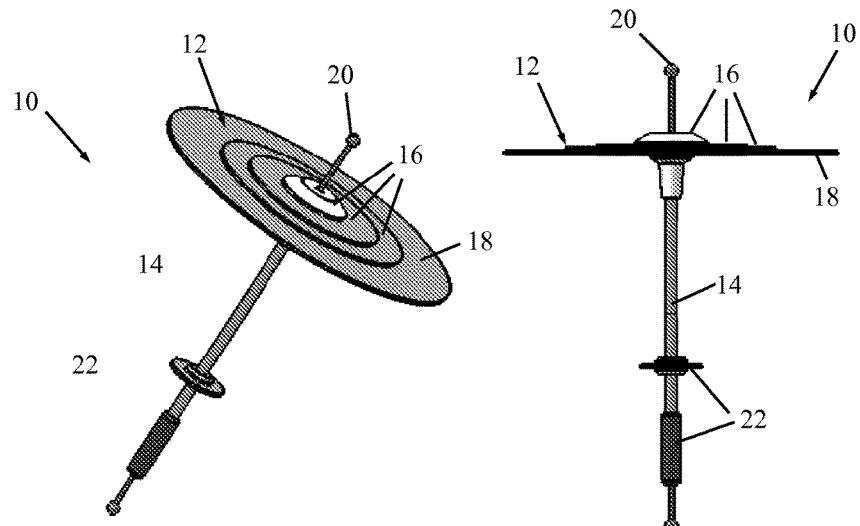
FIG. 1A
FIG. 1B
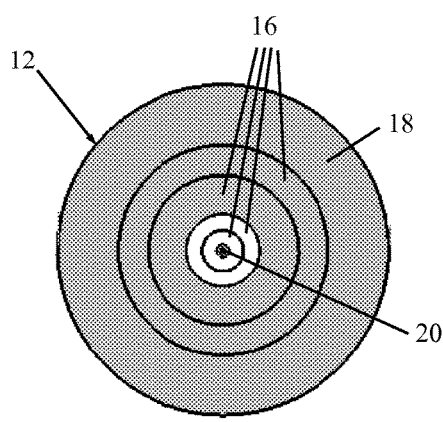
FIG. 1C

OBSTRUCTION DEVICE

FIELD OF THE INVENTION

The present invention generally relates to devices for obstructing or reducing flow through a body lumen, in particular for obstructing or reducing flow of gastric contents across the pyloric valve.

BACKGROUND OF THE INVENTION

Gastroplasty procedures are known for treating obesity, gastroesophageal reflux disease (GERD), cancer, diabetes and the like. Gastric bypass procedures include the well-known Roux-En-Y procedure, as well as other techniques that reduce the size of the stomach and/or form restrictive barriers, alternative paths, pouches and the like in the stomach or other parts of the gastrointestinal tract. These surgical procedures can be performed with endoscopic tools such as a gastroscope, though traditionally they are performed with open or minimally invasive surgery devices.

In the prior art, when an occlusion of the pylorus is required in the course of a gastroplasty procedure or in a procedure that involves the duodenum, the surgeon staples the pylorus shut (in the stomach) and this is a short term occlusion to allow the duodenum to recover from an operation. Transpyloric devices have also been proposed, which may partially and/or intermittently obstruct the pylorus, thereby decreasing the flow of gastric contents into the duodenum.

SUMMARY OF THE INVENTION

The present invention seeks to provide an improved device for obstructing or reducing flow through a body lumen, in particular for obstructing or reducing flow of gastric contents across the pyloric valve (pylorus), as is described more in detail hereinbelow. The device is particularly useful in a transoral gastrointestinal procedure, but the invention is not limited to transoral gastroplasty, and may be used in other laparoscopic, endoscopic, or natural orifice procedures in other body lumens.

The present invention is particularly useful to stop the flow of stomach contents in to the proximal gut which includes the duodenum and the initial part of the jejunum. Such a need arises, for example, after creating an alternative path of flow through a gastro-jejunum anastomosis which bypasses the proximal gut. There could be other cases when this need arises, such as after surgery in the duodenum area or in the pancreas or bile outputs to the duodenum. Another indication could be the need to operate endoscopically on the stomach with an inflated stomach. In this case, the plug keeps the inflating air in the stomach and it does not bloat the intestine.

There is thus provided in accordance with an embodiment of the present invention an obstruction device including an obstruction disc mounted on a proximal portion of a shaft, the disc including an inner radial portion and an outer radial portion, wherein the outer radial portion is more bendable than the inner radial portion. For example, the inner radial portion may be more rigid than the outer radial portion.

In accordance with an embodiment of the present invention the shaft includes one or more anchoring members (e.g., rings).

Further in accordance with an embodiment of the present invention the inner radial portion is semi-rigid and the outer radial portion is flexible.

In accordance with an embodiment of the present invention the inner radial portion extends over a greater area than the outer radial portion.

In accordance with an embodiment of the present invention the outer radial portion is at peripheral edges of the disc.

In accordance with an embodiment of the present invention the disc is shaped as a Belleville washer. For example, the Belleville washer may include the outer radial portion alone, or both the inner and outer radial portions.

Further in accordance with an embodiment of the present invention a grasping member is disposed at a proximal portion of the shaft, proximal to the disc.

BRIEF DESCRIPTION OF THE DRAWINGS

The present invention will be understood and appreciated more fully from the following detailed description taken in conjunction with the drawings in which:

FIGS. 1A-1C are simplified pictorial, front-view and top-view illustrations, respectively, of an obstruction device, constructed and operative in accordance with an embodiment of the present invention;

DETAILED DESCRIPTION OF EMBODIMENTS

Figure 2A:
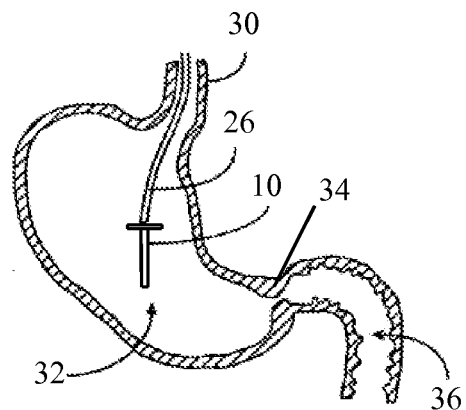
FIGS. 2A-2C are simplified illustrations of introducing the obstruction device of FIGS. 1A-1C into a body lumen (pylorus)

Reference is now made to FIGS. 1A-1C, which illustrate an obstruction device 10, constructed and operative in accordance with an embodiment of the present invention.

Obstruction device 10 includes an obstruction disc 12 mounted on a shaft 14. In accordance with an embodiment of the present invention, disc 12 includes an inner radial portion 16 and an outer radial portion 18, wherein outer radial portion 18 is more bendable than the inner radial portion 16. In one embodiment, the inner radial portion 16 is more rigid than outer radial portion 18. For example, inner radial portion 16 may be semi-rigid and outer radial portion 18 may be flexible. In one embodiment, inner radial portion 16 extends over a greater area than outer radial portion 18; e.g., outer radial portion 18 may be only at the peripheral edges of disc 12 (e.g., with a radial width of less than 2 mm, without limitation). Disc 12 may be impermeable to air or other fluids, depending on the particular need.

Figure 3A:
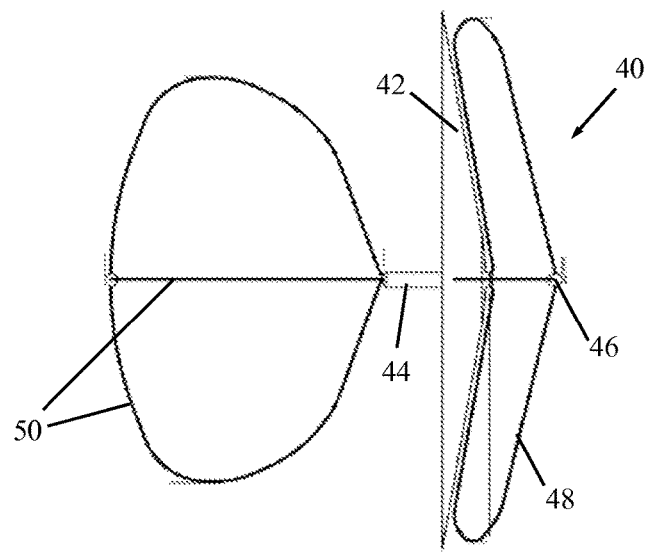
FIGS. 3A-3B are simplified side-view and pictorial illustrations, respectively, of an obstruction device, constructed and operative in accordance with another embodiment of the present invention.
Figure 3B:
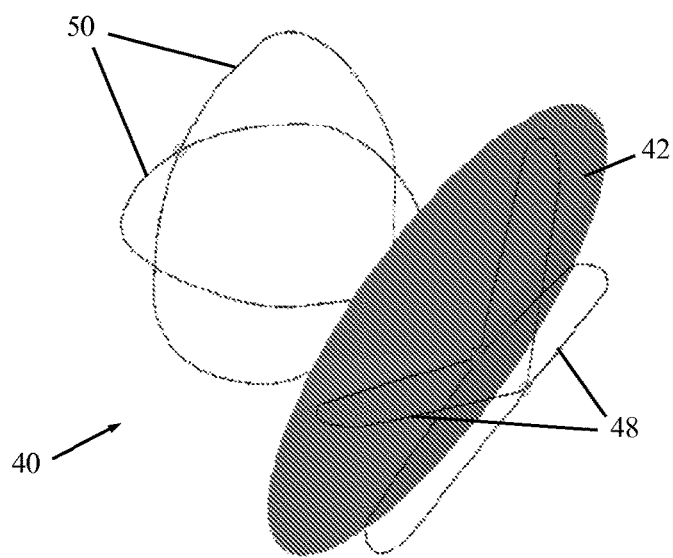

In another embodiment, disc 12 is shaped as a Belleville washer (FIGS. 3A-3B will also illustrate an embodiment wherein the disc is shaped like a Belleville washer). Belleville washers are washers that are generally bowed in the radial direction. Specifically, they have a radial convexity (i.e., the height of the washer is not linearly related to the radial distance, but may, for example, be parabolic in shape). The restoring force of a Belleville washer is proportional to the elastic properties of the material. As a compressive load is applied to a Belleville washer, the forces are directed into a hoop stress that tends to radially expand the washer. This hoop stress is counterbalanced by the material strength of the washer, and the strain of the material causes a deflection in the height of the washer. Stated equivalently, a Belleville washer responds to a compressive load by deflecting compressively, but provides a restoring force that is proportional to the elastic modulus of the material in a hoop stressed condition. Either outer radial portion 18 alone may be the Belleville washer, or inner radial portion 16 may also be part of the Belleville washer.

Materials which may be used in fabricating disc 12 include, without limitation, silicone, silicone elastomers, latex, polyurethane, PTFE (polytetrafluoroethylene), FEP (fluorinated ethylene propylene), and others. In the case of a Belleville washer, medically safe metals may be used, such as but not limited to, stainless steel, nitinol or titanium. Inner radial portion 16 may be made of the same as outer radial portion 18, or of different materials.

Disc 12 can be folded to fit through the esophagus by an endoscopic apparatus. The ability to fold may be due to the flexibility of outer radial portion 18 alone, or the flexibility of both inner and outer radial portions 16 and 18. After reaching the desired destination in the body lumen, such as being seated in the pylorus, disc 12 unfolds and sealingly seats in the lumen.

In the case of a Belleville washer, disc 12 is initially bowed so that the central portion is more proximal than the periphery (or alternatively vice versa the central portion is more distal than the periphery). In this configuration of reduced diameter, the washer can be easily inserted in the lumen. The force of material flowing in the lumen towards the Belleville washer applies a compressive load against the Belleville washer, which causes the Belleville washer to flatten somewhat and increase its overall diameter, thereby sealing the lumen (e.g., pylorus).

Disc 12 is mounted on the proximal portion of shaft 14. In a preferred embodiment, disc 12 is not at the very end of the proximal portion; instead there is a grasping member 20 at the proximal tip of shaft 14, which may be grasped for extracting device 10. Grasping member 20 may be a ball shaped protuberance, for example.

Shaft 14 serves as a distal anchor. In the case of installation in the pylorus, shaft 14 sits in the duodenum. In one embodiment, shaft 14 includes one or more anchoring rings 22, which help keep device 10 in place. In the case of installation in the pylorus, rings 22 may help prevent device 10 from floating back towards the stomach. Without limitation, rings 22 may be made of silicone; shaft 14 may be made of stainless steel or titanium encapsulated in a plastic tube. All parts are of course bio-compatible. In one embodiment, rings 22 are inflatable or expandable (such as by means of a shape memory material).

Figure 2B:
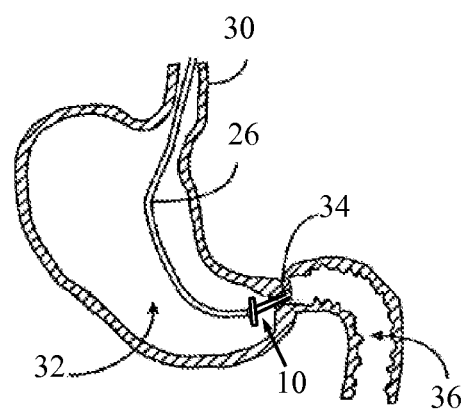
Figure 2C:
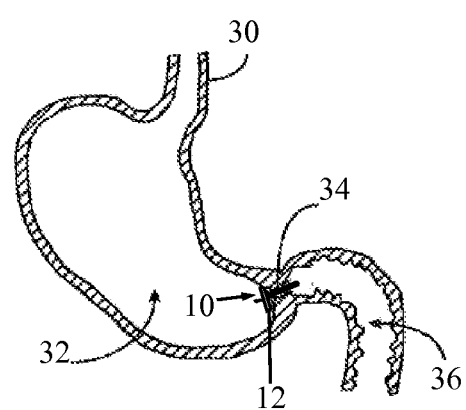

Reference is now made to FIGS. 2A-2C, which illustrate introducing the obstruction device 10 into a body lumen (pylorus).

Obstruction device 10 may be mounted on an endoscopic device 26 and advanced through the esophagus 30 into the stomach 32, as shown in FIG. 2A. As shown in FIG. 2B, disc 12 of device 10 is about to be placed against the inner walls of the pylorus 34 with shaft 14 pointing into the duodenum 36. FIG. 2C shows device 10 anchored in place.

Reference is now made to FIGS. 3A-3B, which illustrate an obstruction device 40, constructed and operative in accordance with another embodiment of the present invention.

Obstruction device 40 includes an obstruction disc 42 mounted on a shaft 44. In accordance with an embodiment of the present invention, obstruction disc 42 is shaped like a Belleville washer. Disc 42 can flex in one direction during insertion and in the opposite direction during retrieval. In another embodiment, obstruction disc 42 has a central, distal apex 46. One or more support struts 48 are disposed on a distal side of obstruction disc 42. One or more anchoring members 50 are disposed on a proximal side of obstruction disc 42. Support struts 48 and anchoring members 50 may be formed of resilient materials, such as but not limited to, NITINOL wire loops or rings, symmetrically placed about apex 46 (i.e., the longitudinal axis of obstruction device 40). The anchoring members 50 are firm enough to anchor device 40 in the GI tract by contacting and gently pressing against the inner walls of the tract, thereby centering and holding device 40 in place without causing stress or damage to the tissue walls. The anchoring members 50 may include a pair of loops which are orthogonal to each other, one being a longitudinal member and the other a latitudinal member. This arrangement is basically self-centering in the GI tract, which helps align the device properly with the pylorus.

The shaft 44 (which may be referred to as the "neck" of the device) not only connects disc 42 to anchoring members 50, but also serves as a spacer between them that allows both parts to be situated well on the mucosa. Shaft 44 can have different lengths and thicknesses depending on the application; for example, in the pylorus the dimensions of shaft 44 are correlated to the usual width of the pylorus muscle.

Support struts 48 may serve as "holding loops" or "grasping loops", which may be held by a grasping tool when inserting the device into the duodenum or other lumen and for retrieval therefrom.

The obstruction device of the present invention can be used in a variety of applications. For example, the obstruction device can be inserted into the colon to block insufflation of air to the proximal colon, such as when performing an ESD (endoscopic submucosal dissection) on the distal colon. In another application, the obstruction device can be deployed in the bronchus of the lungs when taking biopsies or during some endobronchial procedures.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An obstruction device comprising:
   an obstruction disc mounted on a proximal portion of a shaft, said obstruction disc being convexly shaped so as to taper to a smaller diameter towards a distal end of said shaft, a center of said obstruction disc being located at a junction of said obstruction disc and said shaft and a longitudinal axis extends along said shaft passes through said center;
   anchoring members disposed on said shaft on a proximal side of said obstruction disc,
   wherein said anchoring members comprise a pair of loops which are orthogonal to each other, one being a longitudinal member and the other a latitudinal member, and
   one or more support struts disposed on a distal side of said obstruction disc, said one or more support struts comprising one or more loops, each of said one or more loops comprising a first V-shaped portion that is located at the distal side of said obstruction disc, wherein an apex of said first V-shaped portion is located on said longitudinal axis and said first V-shaped portion extends from said center of said obstruction disc to two radially opposing points located at the distal side of said obstruction disc, said first portion curving distally into a second V-shaped portion that is located more distally from the distal side of said obstruction disc than said first V-shaped portion and wherein an apex of said second V-shaped portion is located on said longitudinal axis.

2. The obstruction device according to claim 1, wherein said disc is shaped as a Belleville washer.

3. The obstruction device according to claim 1, wherein said obstruction disc has a central, distal apex.

4. The obstruction device according to claim 1, wherein said one or more support struts comprise a plurality of loops angularly spaced from one another.

5. The obstruction device according to claim 1, wherein said one or more support struts are grasping members.

6. The obstruction device according to claim 1, wherein said disc is capable of flexing in one direction during insertion and in an opposite direction during retrieval.

7. The obstruction device according to claim 1, wherein said shaft serves as a spacer between said anchoring members and said obstruction disc.

\* \* \* \* \*